United States Patent [19]

Hanotier

[11] 4,258,209
[45] Mar. 24, 1981

[54] PROCESS FOR PREPARING TEREPHTHALIC ACID

[75] Inventor: Jacques D. V. Hanotier, Saint-Lambert, Belgium

[73] Assignee: Labofina S.A., Brussels, Belgium

[21] Appl. No.: 68,648

[22] Filed: Aug. 22, 1979

Related U.S. Application Data

[63] Continuation of Ser. No. 947,641, Oct. 2, 1978, abandoned.

[51] Int. Cl.$^3$ ............................................. C07C 51/255
[52] U.S. Cl. ................................................... 562/412
[58] Field of Search ................................ 562/414, 412

[56] References Cited

U.S. PATENT DOCUMENTS

| | | | |
|---|---|---|---|
| 2,833,819 | 5/1958 | Egbert et al. | 562/412 |
| 3,700,731 | 10/1972 | Sullivan | 562/414 |
| 3,852,343 | 12/1974 | Hanotier et al. | 562/412 |

*Primary Examiner*—Alan Siegel
*Attorney, Agent, or Firm*—Schwartz, Jeffery, Schwaab, Mack, Blumenthal & Koch

[57] ABSTRACT

A process for preparing terephthalic acid is disclosed which comprises the steps of oxidizing a substantially homogenous liquid reaction mixture, comprising p-toluic acid, optionally in admixture with p-xylene and partially oxidized p-cylene derivatives, an amount of between 5% and 80% by weight of water, and an oxidation catalyst comprising a catalytically-active metal compound such as manganese compounds, cobalt compounds or mixtures thereof, with an oxygen-containing gas. At least a minimum amount of M millimoles of the catalytically-active metal compound per kg of the liquid reaction mixture is used, wherein M is defined by the following equation (1)

$$M = \frac{y(x + A) + Bx}{Cx + D} \quad (1)$$

wherein
y represents the molar ratio of water/p-toluic acid in the reaction mixture,
x represents the molar ratio of manganese/total amount of manganese + cobalt in the catalyst composition Mn/(Mn+Co),
A equals about 0.200,
B equals about 10.9,
C equals about 4.35; and
D equals about 0.0724.

16 Claims, 1 Drawing Figure

PROCESS FOR PREPARING TEREPHTHALIC ACID

This is a continuation of application Ser. No. 947,641, filed Oct. 2, 1978, now abandoned.

BACKGROUND OF THE INVENTION

This invention relates to an oxidation process, more particularly to a process for preparing terephthalic acid by oxidation of p-toluic acid or mixtures of p-toluic acid with p-xylene and/or with partially oxidized derivatives thereof, such as p-tolualdehyde.

Terephthalic acid is of great commercial importance as it is increasingly used as a starting material for the production of high molecular weight resins such as fiber- and film-forming polyesters.

The prior art teaches many processes for the liquid-phase oxidation of alkyl-substituted aromatic compounds to aromatic carboxylic acids. One of the first patents in this field is U.S. Pat. No. 2,245,528 in the name of Loder, which discloses a one-step process for oxidizing alkylaromatic compounds by molecular oxygen in the presence of a metal catalyst, a solvent such as acetic acid and optionally an oxidation initiator. However, even under severe conditions, the yield in dicarboxylic acids is low. For example, upon oxidizing a mixture of xylenes with air in acetic acid containing cobalt- and manganese acetates as catalysts at 185°–200° C. under a pressure of 50 atmospheres and in the presence of diethylketone as initiator, the yield in phthalic acids was only 2%, and the main reaction products were toluic acids together with other intermediate oxidation products.

A number of further patents disclose processes for the oxidation of p-xylene in one step with improved yields in terephthalic acid. These patents relate mainly to the use of specific activators such as bromine-containing compounds (U.S. Pat. No. 2,833,816), ketones (U.S. Pat. No. 2,853,514), or aldehydes (U.S. Pat. No. 3,036,122). Although some of these processes are applied commercially, they nevertheless suffer from serious drawbacks. For instance, severe corrosion problems arise when bromine-containing activators are used. When a ketone or an aldehyde is employed, part of it is inevitably lost, and the remaining portion is transformed mainly into acetic acid which must be recovered, purified, and commercialized for the process to be economically feasible. Nevertheless, despite those drawbacks, the use of an activator is considered as being an essential requirement for efficiently producing phthalic acids from xylenes.

In most cases, the use of a solvent is also claimed as being necessary. Low-molecular-weight fatty acids, more particularly acetic acid, are widely used for this purpose. The added amount of solvent must be sufficient in order to maintain the reactants and the reaction products in solution or at least in suspension without difficulty. In this way, the reaction mixture is easily agitated, the dispersion of oxygen is improved, the formation of by-products is minimized and the heat of reaction is easily removed by solvent evaporation. However, under the reaction conditions generally used, a significant amount of solvent is lost by co-oxidation. Moreover, the solvent must be separated from the other components of the reaction mixture, and then be purified and recycled. Obviously, this consumption of a part of the solvent and these operations to recover the remaining part result in additional processing costs.

In order to avoid the above-mentioned important problems, it has been suggested to carry out the oxidation of p-xylene in the absence of a solvent. In this case, it is obviously necessary to work at a temperature which is at least in the range of the melting point of p-toluic acid, i.e., about 180° C., in order to obtain a liquid reaction mixture. The choice of temperature is therefore limited. Moreover, in the absence of a solvent, the handling of the reaction mixture as well as the separation and the purification of terephthalic acid are difficult. Generally, the reaction is carried out to the point where the content of terephthalic acid in the mixture does not exceed 60%, preferably 45%, by weight. Beyond this point, "it becomes difficult to handle the oxidation reaction mixture as a slurry, and hence, the operation of the reaction is adversely affected" (see U.S. Pat. No. 3,883,584).

In the absence of a solvent, the removal of the heat of reaction presents another difficulty in industrial scale production, as extensive fouling takes place in the reactor, even when terephthalic acid is not present in large amounts. Thus, in U.S. Pat. No. 2,696,499, which relates to the oxidation of xylene into toluic acids in the absence of a solvent, it is explained that "the essential design problem inherent in the cooling of the xylene oxidation mixture is the prevention of the deposition of solids".

U.S. Pat. No. 3,406,196 describes a two-stage process, wherein water is used as a suspension agent for terephthalic acid. In the first stage, an alkylaromatic compound, more particularly p-xylene, is oxidized by means of air in the absence of any additional solvent into partially oxidized compounds which, in the second stage, are further oxidized at a higher temperature in the presence of substantial amounts of water as a suspending medium. Bromine or a bromine-containing compound must be present to promote oxidation. Nevertheless, very high temperatures in the range of 200° to 275° C. and, more particularly, from 225° C. to 250° C. are required for achieving conversion of those partially oxidized compounds into terephthalic acid. Accordingly, the same or even worse corrosion problems are necessarily encountered than those which are present in processes wherein acetic acid is used as a solvent. Moreover, as stated in said patent, "appreciable losses of unreacted polyalkylaromatic compound by degradation and other side reactions tend to occur when such compounds are exposed to the higher temperatures found necessary for efficient conversion of the partial oxidation products, produced in the first stage of oxidation, to aromatic polycarboxylic acids". Clearly, the teaching of this patent is that the use of large amounts of water, even in the presence of a bromine promoter, does not give satisfactory results for oxidizing p-xylene into terephthalic acid in one step.

Actually, it has been known for a long time already that water is "a catalyst poison in oxidation reaction" (U.S. Pat. No. 2,696,499). According to the most widespread opinion, water has an adverse effect upon the reaction rate by interferring with initiation. As a general rule, its presence is avoided as much as possible, regardless of whether a solvent and/or an activator are present. Thus, U.S. Pat. No. 3,064,044 describes an improved technique for maintaining a final (bromine-promoted) oxidation under substantially anhydrous conditions. In U.S. Pat. No. 3,519,684, which relates to an oxidation process wherein peracetic acid is used as promoter, it is specified that "preferably, nearly anhydrous conditions are employed, although a water content of up to about 10% can be tolerated and a maximum water content of not greater than 5% is preferred". In a continuous process for the oxidation of xylenes in the absence of any promoter and wherein the partially oxidized intermediates are continuously recycled, water is removed from the liquid effluent before recycling the latter in order to retain "the water content in the reaction mixture at less than 15% and preferably less than 5% of the total reaction mixture" (U.S. Pat. No. 3,700,731).

More recently, it has been found that, unexpectedly, the oxidation of p-xylene into terephthalic acid can be carried out in the presence of substantial amounts of water as a solvent, although in the absence of any brominated activator which earlier was considered as an essential requirement. This process is described in the co-pending U.S. Patent Applications Ser. No. 764,981 and Ser. No. 785,827. They comprise oxidizing p-xylene in the liquid phase by an oxygen-containing gas in the presence of p-toluic acid, water and of a heavy metal salt as a catalyst at a temperature of from about 140° C. to about 220° C. under a pressure sufficient to maintain at least a part of the water in the liquid phase. However, as the mutual solubility of p-xylene and water is low at the working temperature, such mixtures of water, p-xylene and p-toluic acid may separate into two phases: an aqueous phase and an organic phase which is rich in hydrocarbon and also contains an important portion of the p-toluic acid which is present in the reaction mixture. In this case, the oxidation reaction takes place mainly in the organic phase where the concentration of water is relatively low. Therefore, the desired solvent effect of water is partly lost. Moreover, this phase separation causes important technical difficulties with regard to homogenization, oxygen dispersion and mass transfer effects.

SUMMARY OF THE INVENTION

It is an object of the present invention to provide a process for oxidizing p-xylene into terephthalic acid by which terephthalic acid is obtained in high yield and good purity, and by which the above-mentioned drawbacks of the prior art processes are avoided.

It is a further object of the present invention to provide such a process which does not require highly corrosion-resistant equipment and can be effected in conventional stainless steel equipment.

It is a further object of the invention to provide such a process which can be performed in the presence of substantial amounts of water without requiring the presence of any additional solvent.

It is a further object of the present invention to provide a process wherein terephthalic acid is prepared by oxidizing a reaction mixture which substantially is a homogenous aqueous solution consisting essentially of the terephthalic acid precursors which are to be oxidized, water, and an oxidation catalyst dissolved therein.

It is a further object of the invention to provide such a process which does not require the use of a promoter such as a bromine compound in addition to an oxidation catalyst.

It is a further object of the present invention to provide such a process wherein the terephthalic acid can easily be recovered from the oxidized reaction mixture at relatively moderate temperatures.

It is a further object of the present invention to provide such a process wherein the catalyst and oxidation intermediates can be recovered and re-used for oxidation.

It is a further object of the present invention to provide such a process wherein terephthalic acid can be produced in an industrial process at relatively low costs.

It is a further object of the invention to provide such a process which can be performed batchwise as well as continuously.

It is a further object of the present invention to provide such a process, wherein the amounts of catalyst, water, and p-toluic which are necessary to secure efficient oxidation of the starting material can easily be calculated.

In order to accomplish the foregoing objects according to the present invention, there is provided a process for preparing terephthalic acid which comprises the steps of:

(a) oxidizing a substantially homogenous liquid reaction mixture comprising at least one oxidizable terephthalic acid precursor selected from the group consisting of p-toluic acid, and mixtures of p-toluic acid and an oxidizable compound selected from the group of p-xylene, partially oxidized p-xylene derivatives, and mixtures thereof;

an amount of at least 5% by weight of water which is sufficient to obtain a workable slurry;

an amount of an oxidation catalyst comprising at least one catalytically active metal compound selected from the group consisting of manganese compounds, cobalt compounds, and mixtures thereof, which is sufficient to provide at least a minimum amount of M millimoles of the catalytically active metal compound per kg of the liquid reaction mixture wherein M is defined by the following equation (1)

$$M = \frac{y(x + A) + Bx}{Cx + D} \quad (1)$$

wherein y represents the molar ratio of water to p-toluic acid in the reaction mixture, x represents the molar ratio of manganese/total amount of manganese+cobalt in the catalyst composition, i.e. Mn/(Mn+Co)

A equals about 0.200,

B equals about 10.9,

C equals about 4.35, and

D equals about 0.0724 with a molecular oxygen-containing gas at a reaction temperature of from about 140° C. to about 220° C. and at a pressure sufficient to maintain at least part of the water in the liquid phase at the reaction temperature; and (b) recovering an oxidized mixture containing the terephthalic acid.

By maintaining the catalyst concentration at at least the above-defined minimum value, an efficient oxidation of any of the above starting material mixtures into terephthalic acid in a homogenous liquid phase reaction mixture is achieved.

Further objects, features, and advantages of the invention will become apparent from the detailed description of the invention and its preferred embodiments which follows when considered together with the accompanying drawing.

BRIEF DESCRIPTION OF THE DRAWING

The attached sheet of drawing represents a phase diagram for mixtures of p-xylene, p-toluic acid and water at a temperature of 185° C.

DETAILED DESCRIPTION OF THE INVENTION AND ITS PREFERRED EMBODIMENTS

It is an important feature of the present invention that the detrimental effect of water, which has been widely recognized in the prior art, can be overcome when the oxidation is performed under the above specific conditions. It is a further feature of this invention that it can be applied to the oxidation of various substrates which may consist of p-toluic acid alone or in admixture with p-xylene and/or partially oxidized derivatives such as p-tolualdehyde. It is still another feature of this invention that such substrates can be oxidized in a homogenous aqueous solution when the amount of catalyst is chosen to correlation with the ratio between the amounts of water and p-toluic acid which are present in the system.

The process according to the present invention may be carried out batchwise or in a continuous procedure. The reactants are dissolved in water and the catalyst is added to the resulting solution. Oxygen is then introduced into this mixture and the oxidation is carried out at a temperature of between about 140° C. and about 220° C. under pressure. The pressure is adjusted in such a manner as to keep the reaction mixture in a substantially liquid phase at the working temperature. Terephthalic acid separates from the reaction mixture as a white crystalline precipitate. In a continuous process, this precipitate is continuously removed by any conventional solid-liquid separation method, such as filtration, centrifugation, or settling and decantation, and the remaining liquid containing unconverted reactants and intermediate oxidation products is recycled into the oxidation zone. Fresh reactants are continuously added to compensate for terephthalic acid thus withdrawn and for the formation of by-products. Thus, no addition of extraneous chemicals is required. Nevertheless, in carrying out the process of the present invention, there may be added to the reaction mixture one or more organic solvents which do not interfere with the reaction and which are relatively inert under the working conditions. Examples of such compounds that can be used as a solvent in admixture with water are benzoic acid and acetic acid. These compounds, which are actually produced in small amounts during the reaction, may, therefore, be allowed to accumulate to some extent in the reaction mixture. However, the advantages resulting from this invention are obtained independently of the presence of such compounds which, when employed, should not be present in an amount exceeding the amount of water in the system.

The amount of water which is suitably used in the process according to the present invention may vary within a wide range, e.g., between about 5 and about 80% by weight of the reaction mixture, depending on different factors. As already emphasized, an essential aspect of the present invention is that the oxidation is carried out in a homogenous aqueous system. Accordingly, the amount of water will primarily be chosen so that it is sufficient to provide for substantially a homogenous aqueous solution of the reactants, taking into account the other process variables such as temperature and the relative amounts of the different compounds to be oxidized. For instance, when the process is applied to the oxidation of p-toluic acid alone or in admixture with other oxygenated compounds which are relatively soluble in water such as p-tolualdehyde, an amount of water will be chosen which is sufficient for completely dissolving the p-toluic acid at the working temperature. As the solubility of p-toluic acid in water steeply increases at increased temperatures, the amount of water to be used may be reduced as the temperature is increased. As a general rule, however, the amount of water will not be lower than 5% and preferably not lower than 10% by weight of reaction mixture.

Figure 1:
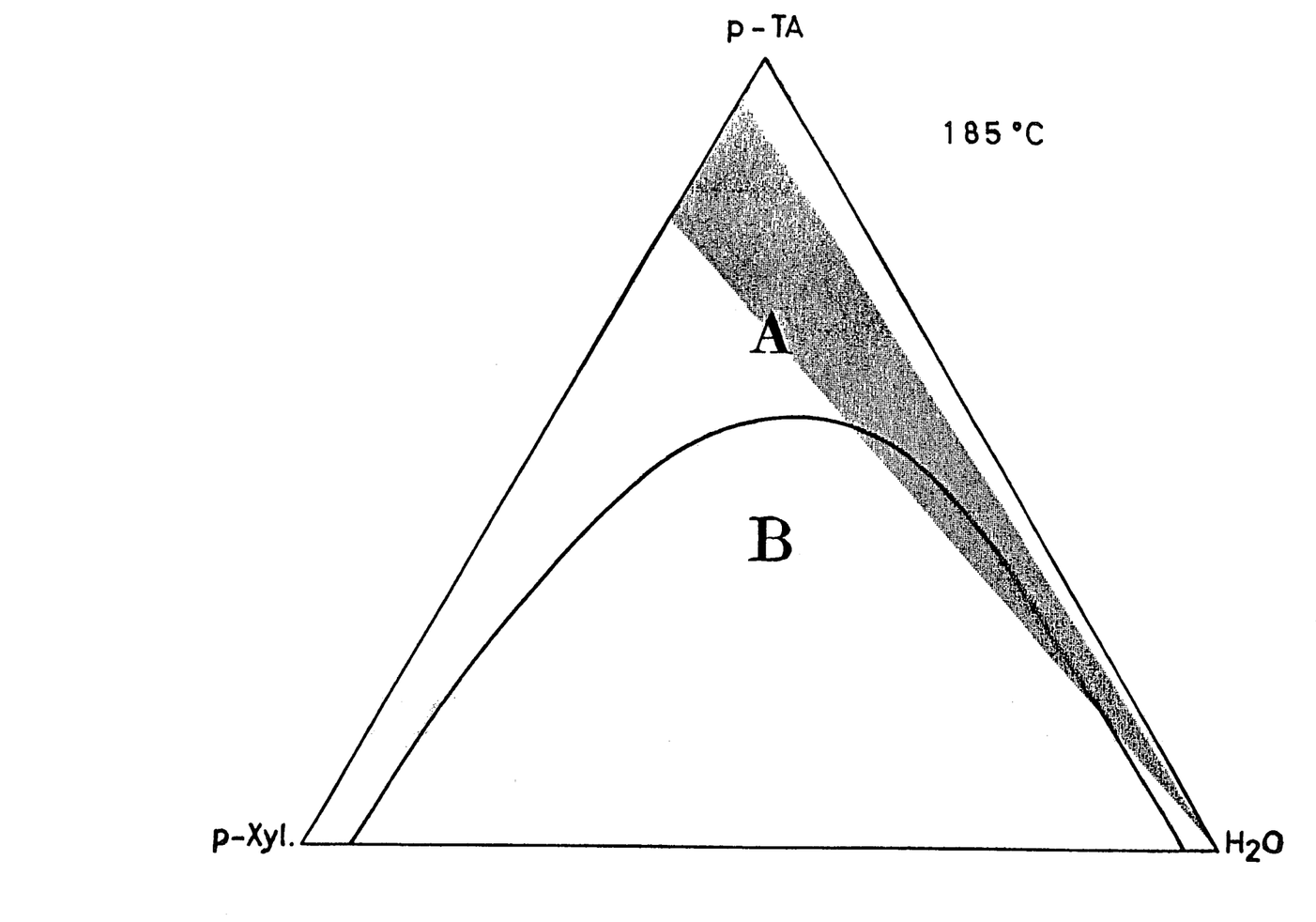

When p-xylene is also a component of the reaction mixture, the amount of water should not exceed an amount beyond which separation of the mixture into two liquid phases would take place. This amount obviously depends on the amount of p-xylene in the mixture. FIG. 1 is a triangular phase diagram for mixtures of p-xylene, p-toluic acid and water at a temperature of 185° C. (in weight %). In this diagram, in Zone A the system is a homogenous solution, and in Zone B it is biphasic. As anvone skilled in the art can easily determine, the boundary line between both of these zones does not vary greatly with temperature. It can be seen that in order to avoid the presence of a substantial organic phase, the amount of p-xylene must be limited. Therefore, when the oxidation of p-xylene according to the process of the present invention is performed batchwise, p-xylene should be added progressively, either intermittently or continuously, to the reaction mixture at such a rate as to maintain the system in zone A. According to a preferred embodiment of the invention, the reaction is performed in a continuous flow-process, whereby unreacted p-xylene together with the intermediate oxidation products, i.e., mainly p-toluic acid, are continuously recycled into the reaction zone. In this case, the molar ratio of p-toluic acid/p-xylene in the reaction mixture at the steady state will be comprised in the range of between about 3 and about 15, depending mainly on the temperature; otherwise stated, the reaction mixture will be comprised in the grey area of the diagram in FIG. 1. It can be seen that this area is almost entirely in Zone A, i.e., corresponds for the main part to homogenous solutions. From the foregoing, it appears that it is always possible to adjust temperature and/or the amount of water used as a solvent in accordance with the present invention in such a manner that a homogenous system is obtained. If the process according to the present invention is carried out in a continuous manner, it is preferable to use the continuous procedure which is described in the co-pending U.S. Application Ser. No. 785,827, filed Apr. 8, 1977, the disclosure of which is hereby incorporated by reference.

But other factors also have to be taken into account. Thus, as terephthalic acid, the desired product, is substantially insoluble in the reaction mixture; an amount of water must be added which is sufficient to obtain a workable slurry. However, there is no advantage in using such a high amount of water that more than, e.g., 10% of terephthalic acid is dissolved at the working temperature. A further factor which has to be taken into account is the reaction rate: although it is possible within the process according to the invention, to carry out the oxidation reaction in a medium comprising as much as 80 wt. percent of water or even more, the presence of an excessive amount of water may adversely affect the reaction rate. Moreover, on some occasions, a part of the catalyst may be diverted from its catalytic function by forming a black compound which precipitates from the oxidation medium. Furthermore, for economic reasons, it is disadvantageous to lose a part of the reactor capacity by using an excessive and needless amount of water. Generally, for these different reasons, the amount of water present in the system will not exceed 75 wt. % and preferably 60 wt. % of the reaction mixture.

Suitably, the oxidation reaction is carried out at a temperature of at least 140° C. Below this temperature, it is difficult to have the reaction mixture as a homogenous solution. On the other hand, working above 220° C. would result in increased overoxidation, undesirable side reactions and corrosion problems. In most cases, the reaction temperature will be between about 150° C. and about 190° C.

The pressure is adjusted as a function of the temperature. A pressure must be employed which is sufficiently high above atmospheric pressure in order to maintain the reaction mixture in a liquid state at the working temperature. A pressure in excess of this value is generally useful for ensuring active oxidation. Generally, the pressure will be comprised between about 5 and about 40 kg/cm$^2$.

The oxidation catalyst used in the process of the present invention may be a heavy metal compound composition comprising at least one metal compound selected from the group of manganese compounds, cobalt compounds, or mixtures thereof, provided it is at least partially soluble in the aqueous reaction mixture or is capable of forming a soluble or at least partially soluble compound with one of the reactants in this mixture. The metal compounds which can be employed in the catalyst composition, suitably are salts. In particular the salts of carboxylic acids are preferred, e.g., acetates, naphtenates, toluates, and the like. Further to cobalt and/or manganese compounds, the catalyst composition may comprise compounds, in particular carboxylic acid salts, of other metals which are conventionally used in oxidation catalysts.

A fundamental aspect of the present invention is that the minimum concentration of catalyst, which is necessary for ensuring oxidation in a homogenous aqueous system, depends upon the respective amounts of water and p-toluic acid in said system. As a matter of fact, in a homogenous aqueous solution of p-toluic acid and optionally p-xylene and/or partially oxidized derivative(s) thereof, oxidation cannot take place when the amount of active catalyst is lower than a critical concentration M in millimoles of the metal compound per kg of reaction mixture given by the following equation (1)

$$M = \frac{y(x + A) + Bx}{Cx + D} \quad (1)$$

where
y is the molar ratio of water to p-toluic acid;
x is the amount of manganese in the metal catalyst in parts by mole relative to the total amount of manganese and cobalt therein, i.e., Mn/(Mn+Co);
A = about 0.200;
B = about 10.9;
C = about 4.35; and
D = about 0.0724.

The quantities A, B, C, and D, as given hereinabove, are the result of experimental determinations and therefore are subjected to measurement errors. It has been computed that these quantities with their confidence limits are respectively
A = 0.200±0.031; B = 10.9±1.3; C = 4.35±0.17; and D = 0.0724±0.0117.

Consequently, the value of M as calculated by means of equation (1) for a given value of y and x has to be considered as an estimate of the actual critical concentration which, in terms of statistics, is comprised within a confidence interval centered on M. As those skilled in the art will realize, this confidence interval depends on the values of y and x used in the calculation of M, but for each particular case, it can be calculated from the above data by application of Taylor's formula. Thus, for example, the critical concentration of catalyst will be comprised within the confidence intervals 21.46±0.81 when y=70 and x=1.0
and
2.74±0.45 when y=1 and x=0.5.

The critical concentration of catalyst as defined hereabove is the lowest concentration that can be used under given conditions. At lower amounts, the process will not operate. Obviously, it is preferred in practice to use an amount of catalyst higher than this minimum. As a matter of fact, the rate of oxidation increases as the concentration of catalyst is increased. However, concentrations of catalyst higher than about 40 millimoles of metal compound per kg of reaction mixture are not advantageous for economic considerations. Suitably, the catalyst will be used in an amount which is comprised between a value slightly higher than the minimum M as calculated from equation (1) and about 30 millimoles per kg of reaction mixture.

As it can be seen from equation (1), the critical concentration of catalyst increases if the concentration of water is increased and the concentration of p-toluic acid is decreased. Otherwise stated, oxidation cannot take place in such an aqueous solution unless the concentration of p-toluic acid is above a critical value which increases as the concentration of catalyst is decreased. Thus, not only the catalyst but also p-toluic acid are essential for allowing oxidation to take place in the presence of substantial amounts of water. Actually, due to the combined action of the catalyst and of p-toluic acid, both used in proper amounts in accordance with the present invention, it is possible to oxidize p-xylene into terephthalic acid without resorting to the use of costly and/or corrosive activators, such as brominated compounds. This effect of p-toluic acid is a quite unexpected aspect of the present invention as other carboxylic acids, even acids of similar structure, such as benzoic acid, do not exhibit the same property.

Furthermore, it is apparent from equation (1), that the critical minimum concentration of catalyst which is necessary for ensuring oxidation to take place in a homogenous aqueous system also depends on the relative proportions of manganese and cobalt compounds within the employed catalyst. It can be seen that manganese is markedly more effective than cobalt. For instance, for allowing oxidation to take place in a 50 wt. % aqueous solution of p-toluic acid (molar ratio water to p-toluic acid=7.56), the minimum concentration of catalyst, which is needed, is 4.5 or 20.9 millimoles/kg according to whether manganese or cobalt is used as sole catalyst. For practical reasons, however, it is advantageous to employ a mixture of both metals, as cobalt generally exerts a beneficial effect upon the reaction rate. Moreover, it has been observed that when a mixture of manganese and cobalt compounds is employed as a catalyst, less overoxidation takes place and higher yields in terephthalic acid are generally obtained than when each metal is employed solely. For example, the combustion ratio (the mole ratio of carbon dioxide evolved per oxygen absorbed) generally has a value between 0.06 and 0.09 in the first case, whereas values of about 0.15 are observed in the second case. Actually, this beneficial effect of using conjointly manganese and cobalt as catalyst is a typical feature and a further advantage of the present invention: when the reaction is carried out in a biphasic system instead of a homogenous solution as in the present process, combustion ratios of 0.12 or even more are regularly observed regardless of whether manganese or cobalt or mixtures thereof are used. In most cases, a value of x in equation (1) of between about 0.1 and about 0.9 will be used with advantage to ensure active oxidation in a homogenous aqueous medium and high yields in terephthalic acid.

For the same practical reason as hereabove, it may also be advantageous if in addition to cobalt and/or manganese the catalyst comprises a further metal component such as nickel, lead, or cerium. Although such other metals are not essential for allowing oxidation to take place in a homogenous aqueous medium, they may afford some practical improvement with respect to, e.g., product purity and reaction rate.

A surprising feature of the present invention is that the minimum concentration of catalyst to be used for ensuring oxidation in aqueous medium can be calculated from equation (1) for any composition of the reaction mixture; and this equation is independent of such important operating variables as temperature. This is illustrated by the results shown in Table 1 wherein values of M experimentally obtained over a wide range of conditions are compared with the values calculated from equation (1). Most of these results were obtained by the following experimental method.

Into a one-liter corrosion-resistant autoclave equipped with a mechanical agitation device, a heating jacket, a gas inlet tube, a vent, and a metering pump for injecting a liquid, there are charged the different components to be present in the oxidation reaction mixture, i.e., p-toluic acid, water, and the catalyst. This mixture is then heated while stirring and passing air therethrough. Once oxidation has started, an aqueous solution of the catalyst having the same catalyst concentration as the initial reaction mixture is progressively inducted into the mixture. As a result, the reaction mixture is progressively diluted with water without any variation of the catalyst concentration. p-Xylene may also be present in the initial mixture provided that its concentration is such that no phase-separation takes place upon dilution of the reaction mixture with the aqueous catalyst solution.

The degree of oxidation is observed by measuring continuously the oxygen content of the exhaust gas by means of an oxygen analyzer. As long as the concentration of p-toluic acid in the system is sufficiently high in order to ensure an efficient oxidation at the chosen catalyst concentration, the reaction proceeds regularly at a rate which decreases progressively as a result of dilution. However, as soon as the critical concentration of p-toluic acid is reached, the reaction rate falls rapidly down to almost nil. Then, injection is discontinued and the reaction mixture is analyzed. The molar ratio of water to p-toluic acid thus determined is obviously the critical y value corresponding to the given concentration M of catalyst or, conversely, M is the minimum concentration of catalyst to be used for ensuring oxidation in a reaction mixture wherein the ratio between water and p-toluic acid is given as y. Actually, M still depends on the composition of the catalyst which may be expressed as the molar ratio of manganese to the total amount of manganese and cobalt in the used catalyst composition (x in equation 1).

Obviously, such determinations are subject to experimental errors so that, for a given reaction mixture (for a given y and x), different values of $M_i$ are expected to be obtained which will statistically be distributed around the actual value with a standard deviation o. Values of $M_i$ thus determined for different $y_i$ and $x_i$ are shown in the following table. From these data, it can be estimated that the standard deviation of $M_i$ from the value M as calculated in equation (1) is 0.70. Accordingly, any experimental value $M_i$, which does not differ from the calculated one by more than two standard deviations, i.e., by more than 1.4, can be considered as consistant with equation (1).

From the results given in Table I, it appears clearly that:

(1) Equation (1) is valid for any value of y and x (compare for instance experiments no. 1 and 7 for y and experiments no. 7 and 19 for x).
(2) Equation (1) is independent of the presence or absence of p-xylene (compare for instance experiments no. 8 and 13).
(3) Equation (1) is independent of temperature (compare for instance experiments no. 3 and 9).
(4) Equation (1) is independent of the presence of metals other than manganese and cobalt (compare for instance experiments no. 2 and 5).

TABLE 1

| No. | Temperature | Reaction mixture (wt %) | | | | | M | |
|---|---|---|---|---|---|---|---|---|
| | | p-xylene | p-toluic acid | water | y | x | observed | calculated |
| 1 | 185 | 0.3 | 9.7 | 90.0 | 70.22 | 1.00 | 20.1 | 21.5 |
| 2 | 185 | 0.5 | 20.0 | 79.5 | 30.08 | 1.00 | 10.1 | 10.6 |
| 3 | 185 | 1.5 | 45.7 | 52.8 | 8.76 | 1.00 | 5.1 | 4.8 |
| 4 | 170 | 0.4 | 10.6 | 89.0 | 63.54 | 1.00 | 20.0 | 19.7 |
| 5 | 170 | 0.6 | 23.5 | 75.9 | 24.38 | 1.00 (1) | | 9.0 | 9.1 (1) |
| 6 | 170 | 1.4 | 43.5 | 55.1 | 9.60 | 1.00 | 5.1 | 5.1 |
| 7 | 170 | 0.1 | 61.3 | 38.6 | 4.76 | 1.00 | 3.7 | 3.8 |
| 8 | 170 | 11.6 | 76.6 | 11.8 | 1.17 | 1.00 | 3.1 | 2.8 (2) |
| 9 | 160 | 1.3 | 42.6 | 56.1 | 9.95 | 1.00 | 5.1 | 5.2 |
| 10 | 170 | 1.3 | 44.4 | 54.3 | 9.25 | 0.79 | 5.2 | 5.1 |
| 11 | 170 | 0.3 | 23.0 | 76.7 | 25.21 | 0.50 | 10.1 | 10.3 |
| 12 | 170 | 0.2 | 10.8 | 89.0 | 62.34 | 0.46 | 21.7 | 22.2 |
| 13 | 170 | 0.0 | 41.8 | 58.2 | 10.53 | 0.46 | 5.5 | 5.8 |
| 14 | 160 | 0.5 | 43.9 | 55.5 | 9.57 | 0.46 | 5.5 | 5.5 |
| 15 | 170 | 0.5 | 24.3 | 75.2 | 23.46 | 0.33 | 10.1 | 10.6 |
| 16 | 170 | 0.3 | 27.0 | 72.7 | 20.39 | 0.25 | 10.1 | 10.2 |
| 17 | 170 | 0.4 | 30.4 | 69.2 | 17.23 | 0.17 | 10.1 | 10.1 |
| 18 | 170 | 0.5 | 35.3 | 64.2 | 13.77 | 0.09 | 10.1 | 10.7 |
| 19 | 170 | 5.4 | 60.5 | 34.1 | 4.27 | 0.00 | 11.7 | 11.8 |
| 20 | 170 | 0.8 | 74.9 | 24.3 | 2.45 | 0.00 | 6.1 | 6.8 |
| 21 | 170 | 0.0 | 81.4 | 18.6 | 1.73 | 0.00 | 3.9 | 4.8 |

(1) An equimolecular mixture of manganese and nickel acetates used as catalyst. The calculation of x and M are made without taking nickel into account.
(2) Value obtained without dilution of the reaction mixture. The critical ratio of water to p-toluic acid was reached spontaneously, by consumption of the latter and production of the former as a result of oxidation.

The teaching of the prior art concerning the selection of the metal compound to be used for oxidizing p-xylene and its partially oxidized derivatives to terephthalic acid is somewhat confusing. As a general rule however, cobalt is claimed to be the best catalyst, especially in the absence of a brominated activator, and manganese to be less active if not inactive. For the oxidation of p-toluic acid, manganese has been shown to be inactive (N. Ohta et al., Chem. Abstr. 56, 8620 g, 1962) or even inhibitory (V.N. Aleksandrov et al., Kinet. Katal. 15, 505, 1974). In other circumstances, manganese exhibits catalytic activity but discoloration of terephthalic acid takes place when the content of water is higher than 10% by weight of the solvent or when the content of manganese in the reaction mixture is high. It is therefore highly unexpected that in the process of the present invention, manganese has an outstanding activity for allowing the oxidation reaction to take place in the presence of large amounts of water and that terephthalic acid is obtained in high yield as a white cristalline precipitate which is especially suitable for further purification up to the degree of purity which is required for the production of polyester fibers (=fiber-grade).

The invention will now be described by the following examples which are given for the purpose of illustration and are not intended to limit the scope of the invention.

EXAMPLE 1

Into a corrosion-resistant autoclave of one-liter capacity equipped with a mechanical agitation device, a heating jacket, a gas inlet tube and a vent, there were charged:
  p-xylene: 45.0 g
  p-toluic acid: 187.5 g
  various oxygenated p-xylene derivatives: 4.5 g
  water: 63.0 g
  manganese acetate: 1.50 millimoles
  cobalt acetate: 1.74 millimoles.

The reactor was pressurized with air up to a pressure of 20 kg/cm$^2$ and the above mixture was heated while stirring and admitting air at a flow rate of 92 liters per hour.

In the above charge, the molar ratio of water to p-toluic acid (y) was $(63.0 \times 136.15)/(18.02 \times 187.51) = 2.54$ and the molar ratio Mn/Mn+Co in the catalyst (x) was: $1.50/(1.50+1.74)=0.46$. By application of equation (1), the minimum concentration of catalyst which was necessary in this case for ensuring oxidation is calculated as follows:

$$M = \frac{2.54\,(0.46 + 0.200) + 10.9\,(0.46)}{4.35\,(0.46) + 0.0724} = 3.2 \text{ millimoles/kg}.$$

Actually, in the present example, the concentration of catalyst was 10.8 millimoles/kg, i.e., about three times the minimum amount. As a matter of fact, the reaction started spontaneously upon heating and took place actively; as a result, the temperature increased rapidly, it was maintained at 170° C. by controlled cooling.

After a reaction period of 180 minutes, the oxygen absorption amounted to 40.9 liters (measured at room temperature and a pressure of one atmosphere). The admission of air was then discontinued and the reactor was progressively depressurized in order to recover unreacted p-xylene by stripping with water. The reactor was finally cooled and opened. The precipitate contained therein was filtered, washed with water and dried under vacuum at about 80° C. Then it was analyzed by a combination of methods comprising acidimetry, polarography and vapor-phase chromatography. It was thus determined that 89.4% of the p-xylene fed and 23.1% of the p-toluic acid fed had been transformed into the following products:
  terephthalic acid: 90.2 g
  4-carboxybenzaldehyde: 8.8 g
  other intermediates: 3.8 g
  heavy by-products: 2.2 g Taking into account that 4-carboxybenzaldehyde and other intermediate products would in fact be recycled in a continuous process and the major portion thereof would ultimately be transformed into terephthalic acid, it can be estimated that the yield in the terephthalic acid in such a continuous process would amount to more than 90 mole %, based on the amount of p-xylene consumed.

In another operation performed under the same conditions, the hot reaction mixture was submitted to filtration: the resulting cake was further washed on the filter with hot water and dried under vacuum. Analysis of the dried product shows that it consists of (in % by weight):
  terephthalic acid: 85.6%
  p-toluic acid: 9.6%
  4-caboxybenzaldehyde: 3.6%

The color of this sample was determined by measuring the optical density of a solution thereof in diluted ammonia, according to a method described in U.S. Pat. No. 3,354,802, except that a 5 cm cell is used instead of a 4 cm cell. The values of optical density thus obtained were given in the following Table II and were compared with the values of optical density which are obtained with a sample of commercial terephthalic acid of 99+% purity.

TABLE II

| CRUDE SAMPLE | | OPTICAL DENSITY AT (mu): | | |
|---|---|---|---|---|
| ORIGIN | PURITY (wt%) | 340 | 380 | 400 |
| Prepared by the process according to the present invention | 85.6 | 0.428 | 0.102 | 0.076 |
| Commercial product | 99+ | 0.726 | 0.183 | 0.111 |

It can be seen that the crude sample obtained in this process by simple filtration and superficial washing has better color characteristics than a commercial sample of terephthalic acid of much better purity. This crude sample is therefore especially suitable for further purification up to the fiber quality.

EXAMPLE 2

The experiment as in the preceding example was repeated except that instead of 63.0 g of water there was used as a solvent a mixture of:
  water: 33.0 g
  acetic acid: 30.0 g After 180 minutes of reaction, the oxygen absorption amounted to 39.7 liters, i.e., about the same amount as in the preceding example. The reaction mixture was then treated and analyzed as described in the preceding example. It was thus determined that 88.0% of the p-xylene fed and 23.5% of the p-toluic acid fed had been transformed into the following products:
  terephthalic acid: 89.4 g
  4-carboxybenzaldehyde: 6.5 g
  other intermediates: 4.8 g
  heavy by-products: 3.2 g By the same method as in the preceding example it can be estimated that in a continuous process working under the conditions used in this example, the yield in terephthalic acid would be about 90 mole % based on p-xylene consumed.

As can be seen, these results are practically identical to those of the preceding example where water was used as sole component of the solvent.

EXAMPLE 3

The experiment of Example 2 was repeated except that formic acid was substituted for acetic acid. The solvent used in this case was therefore a mixture of:
water: 33.0 g
formic acid: 30.0 g After 180 minutes of reaction, the oxygen absorption amounted to 36.7 liters. By the same analytical procedure as in the preceding examples, it was determined that 88.0% of the p-xylene fed and 15.6% of the p-toluic acid fed had been transformed into the following products:
terephthalic acid: 66.7 g
4-carboxybenzaldehyde: 6.8 g
other intermediates: 7.0 g
heavy by-products: 3.7 g By the same method as in the present example, it can be estimated that in a continuous process, working under the conditions of the present example, the yield in terephthalic acid would be about 85 mole % based on p-xylene consumed.

Although these results are not quite as good as those of the preceding examples, they show that large amounts of formic acid can be tolerated in the reaction mixture without serious detrimental effects upon the yield and the rate of the reaction. This is especially unexpected as in the prior art formic acid has always been described as a potent inhibitor of oxidation reactions. As formic acid is always produced in such reactions, elaborate and expensive procedures have generally to be designed for avoiding any accumulation thereof in the reaction mixture. In the present process, formic acid is burned as attested by the fact that carbon dioxide evolved in this experiment was 6.0 liters instead of 3.8 liters as measured in the experiment of example 1. Accordingly, in the process of the present invention, no special operation is needed for removing formic acid from the reaction mixture.

EXAMPLE 4

The experiment of example 1 was repeated except that cobalt was used as sole catalyst. The actual charge was the following:
p-xylene: 45.0 g
p-toluic acid: 190.1 g
various oxygenated derivatives: 1.9 g
water: 63.0 g
cobalt acetate: 3.48 millimoles.

In this charge, y was 2.50 and obviously x was 0.00. Accordingly, the limiting amount of cobalt to ensure oxidation in this case was $$M = \frac{2.50 \, (0.200)}{0.0724} = 6.9 \text{ millimoles/kg.}$$

The concentration of cobalt acetate in the initial mixture was 11.6 mmoles/kg, thus about twice the limiting amount. After 180 minutes of reaction, the oxygen absorption amounted to 41.5 liters. The reaction mixture was then treated and analyzed as already described. It was thus determined that 90.8% of the p-xylene fed and 19.5% of the p-toluic acid fed had been transformed into the following products:
terephthalic acid: 74.2 g
4-carboxybenzaldehyde: 6.8 g
other intermediates: 1.5 g
heavy by-products: 3.7 g By comparing these results with those of example 1, it can be seen that less terephthalic acid was produced although the oxygen absorption was slightly higher. As a matter of fact, by estimating as in the preceding example the yield in terephthalic acid that would be achieved in a continuous process, a value of 81% is obtained instead of 90%. This difference clearly shows the yield advantage resulting from using as catalyst a mixture of manganese and cobalt instead of cobalt alone.

EXAMPLE 5

The experiment of example 1 was repeated except that here it is manganese which was used as sole catalyst. The actual composition of the charge was the following:
p-xylene: 45.0 g
p-toluic acid: 182.2 g
various oxygenated derivatives: 9.2 g
water: 63.0 g
manganese acetate: 3.00 millimoles.

In this charge, y was 2.60 and obviously x was 1.00. Accordingly, the limiting amount of manganese to ensure oxidation was $$M = \frac{2.60 \, (1.00 + 0.200) + 10.9}{4.35 + 0.0724} = 3.2 \text{ millimoles/kg.}$$

In the present example, the concentration of manganese was 10.0 millimoles/kg, i.e., about three times the limiting amount as in example 1.

After 180 minutes of reaction, the oxygen absorption was 25.3 g liters, i.e., markedly lower than in the preceding examples. The reaction mixture was then treated and analyzed as already described. It was thus determined that 70.2% of the p-xylene fed and 5.8% of the p-toluic acid fed has been transformed into the following products:
terephthalic acid: 31.2 g
4-carboxybenzaldehyde: 5.9 g
other intermediates: 6.3 g
heavy by-products: 5.1 g By comparing these results with those of examples 1 and 2, it appears clearly that less reactants were consumed here and that less terephthalic acid was produced. Moreover, the yield in terephthalic acid of a continuous process estimated from these data as in the preceding examples amounts to only 69%. Thus, although manganese is markedly more efficient than cobalt to ensure oxidation in the presence of water (as attested by the lower value calculated for M by comparison with the value calculated for cobalt alone), there is a definite advantage with respect to both the rate and the yield of the reaction to use manganese in association with cobalt as in example 1.

EXAMPLE 6

The experiment of example 1 was repeated except that in this case manganese was used in association with nickel. The actual composition of the charge was the following:

p-xylene: 45.0 g
p-toluic acid: 182.8 g
various oxygenated derivatives: 9.2 g
water: 63.0 g
manganese acetate: 1.50 millimoles
nickel acetate: 1.50 millimoles.

In this charge, y was 2.60 and x was 1.00 as in the preceding example, thus M was 3.2 millimoles/kg (nickel is not taken into account in the calculation of M). In the present example, the concentration of manganese was 5.0 millimoles per kg, thus 1.8 in excess over the limiting amount. As a matter of fact, oxidation took place actively.

After 180 minutes, the oxygen absorption amounted to 29.2 liters and the reaction mixture was analyzed as already described. It was thus found that 79.1% of the p-xylene fed and 3.3% of the p-toluic acid fed had been transformed into the following products:
   terephthalic acid: 35.6 g
   4-carboxybenzaldehyde: 6.6 g
   other intermediates: 2.6 g
   heavy by-products: 3.2 g By comparing these results with those of the preceding example, it can be seen that somewhat more oxygen was absorbed and more terephthalic acid was produced than when manganese was used alone at a concentration twice as high as in the present example. This shows that other metals than cobalt can be used in association with manganese to improve the rate of the reaction.

EXAMPLE 7

Into the same autoclave as in the preceding examples, there was charged:
   p-xylene: 45.0 g
   p-toluic acid: 218.5 g
   various oxygenated derivatives: 6.5 g
   water: 30.0 g
   manganese acetate: 0.52 millimoles
   cobalt acetate: 0.45 millimoles.

In this charge, the mole ratio of water to p-toluic acid(y) was 1.04 and the mole fraction of manganese in the catalyst (x) was 0.46. By application of equation (1), the minimum concentration of catalyst to be used in this case to ensure oxidation is therefore M=2.7 millimoles/kg. Actually, in the present example, the concentration of catalyst was 0.97 millimoles for 300 g of initial mixture or 3.2 millimoles/kg, i.e. by only 0.5 millimoles in excess over the limiting amount. Nevertheless, oxygen absorption started spontaneously and took place actively; as a result, the temperature increased rapidly and was maintained at 170° C. by controlled cooling.

After 395 minutes of reaction, 62.9 liters of oxygen had been absorbed. The admission of air was then discontinued and the same procedure as in Example 1 was applied for determining the composition of the reaction mixture. It was thus established that 98.8% of the p-xylene fed and 29.2% of the p-toluic acid fed had been transformed into the following products:
   terephthalic acid: 102.5 g
   4-carboxybenzaldehyde: 6.6 g
   other intermediates: 4.6 g
   heavy by-products: 3.6 g.

By estimating from these data, as in Example 1, the yield in terephthalic acid that would be achieved in a continuous process where the intermediates are recycled, there is obtained a value of 80%, i.e., by 10% lower than the yield estimated in Example 1. The main difference between both experiments is that in Example 1 the water content of the charge was 21 wt % as compared with only 10% in the present case. The resulting difference in the yield may thus be considered as a further illustration of the advantage of carrying out the oxidation of p-xylene in the presence of substantial amounts of water, in accordance with the present invention.

COMPARATIVE EXAMPLE

The same amounts of compounds as in the preceding example were charged into the autoclave except that only 0.30 millimole of manganese acetate and 0.35 millimole of cobalt acetate were used. The total concentration of metal catalyst was therefore 2.2 millimoles/kg, i.e. by 0.5 millimoles lower than the limiting amount as calculated in the preceding example.

Upon heating the mixture in the presence of a stream of air under the same conditions as in the preceding example, oxygen absorption started similarly but after about 70 minutes fell suddenly down to a negligible level. Oxygen absorption amounted to only 6.7 liters.

EXAMPLE 8

Into the same autoclave as in Example 1, there was charged
   p-tolualdehyde: 45.0 g
   p-toluic acid: 187.5 g
   various oxygenated derivatives: 4.5 g
   water: 63.0 g
   manganese acetate: 1.50 millimoles
   cobalt acetate: 1.74 millimoles.

As it can be seen, this mixture was very close to those charged in Examples 1 to 5 except that p-tolualdehyde was substituted for p-xylene. The molar ratio of water to p-toluic acid was again 2.54. Thus, by application of equation (1), the minimum concentration of catalyst to be used for ensuring oxidation is M=3.2 millimoles/kg. Actually, in the present example, the concentration of catalyst was 10.8 millimoles/kg, i.e. about three times as high.

This mixture was heated in the presence of air as in the preceding examples. Oxygen absorption started spontaneously at about 30° C. Temperature was allowed to increase and was maintained at 170° C. by controlled cooling. After 180 minutes of reaction, the oxygen absorption amounted to 25.6 liters. The admission of air was then discontinued, 180 ml of n-heptane was injected into the reactor for extracting unreacted p-tolualdehyde while continuing stirring and heating. The resulting mixture was then cooled and the reactor was opened. The precipitate contained therein was filtered, washed with n-heptane, dried under vacuum at 50° C., washed again with water and finally dried under vacuum at about 70° C. It was then analyzed by the same procedure as in the preceding examples. The filtrate and washing were combined and the heptane extract was separated by decantation. An aliquot part of this extract was analyzed by vaporphase chromatography to determine unreacted p-tolualdehyde. The remaining part was evaporated under vacuum up to dryness and the residue was analyzed by the same method as the first precipitate.

From those different analyses, it was determined that 99.9% of the p-tolualdehyde fed and 10.7% of the p-toluic acid fed had been transformed into the following products:
   terephthalic acid: 58.4 g 4-carboxybenzaldehyde: 7.1 g
other intermediates: 6.1 g
heavy by-products: 5.4 g

COMPARATIVE EXAMPLE 1

The same amounts of compounds as in the preceding example were charged into the autoclave except that only 0.3 millimoles of both manganese and cobalt acetates were used. The total concentration of catalyst was therefore 2.0 millimoles/kg, i.e. by 1.2 millimoles lower than the limiting amount as calculated by equation (1).

This mixture was heated in the presence of air under the same conditions as in the preceding example. After 180 minutes of reaction, the oxygen absorption amounted to only 9.0 liters. The reaction mixture was then treated and analyzed as in the preceding example. It was thus determined that the p-tolualdehyde fed had been completely transformed into the following products:
  terephthalic acid: 2.3 g
  p-toluic acid: 31.7 g
  4-carboxybenzaldehyde: 3.8 g
  other intermediates: 0.9 g
  heavy by-products: 2.0 g It can be seen that in the present case p-tolualdehyde has been mainly transformed into p-toluic acid without significant formation of terephthalic acid.

COMPARATIVE EXAMPLE 2

In this example, p-tolualdehyde was used as sole substrate to be oxidized. The actual charge was the following:
  p-tolualdehyde: 225.0 g
  water: 75.0 g
  manganese acetate: 1.50 millimoles
  cobalt acetate: 1.50 millimoles.

Upon heating this mixture in the presence of air under the same conditions as in Example 8, oxygen absorption started similarly but then slowed down markedly. After about 240 minutes of reaction at 170° C., the oxygen absorption amounted to 29.6 liters. By treating and analyzing the resulting reaction mixture as described above, it was determined that 99.7% of the p-tolualdehyde fed had been transformed into the following products:
  terephthalic acid: 4.6 g
  p-toluic acid: 171.4 g
  4-carboxybenzaldehyde: 4.6 g
  other intermediates: 1.3 g
  heavy by-products: 1.3 g.

It can be seen that, here again, p-toluic acid was the main product from the oxidation of p-tolualdehyde and that only small amounts of terephthalic acid has been formed. This result strikingly illustrates that to oxidize p-tolualdehyde into terephthalic acid in accordance with the present invention, p-toluic acid must be present in sufficient amount from the beginning of the reaction.

EXAMPLE 9

The experiment of Example 8 was repeated except that 3.48 millimoles of cobalt acetate were used as sole catalyst. By application of equation (1), it can be calculated that the minimum concentration of cobalt to be used in this case is $M=7.0$ millimoles/kg. Actually, the concentration of cobalt catalyst in the present example was 11.6 millimoles/kg.

Here again, oxygen absorption started at low temperature. Nevertheless, heating was so applied as to maintain a temperature of 170° C. After about 210 minutes of reaction, the oxygen absorption amounted to 20.8 liters. The reaction mixture was then treated and analyzed as in the preceding example. It was thus determined that 99.9% of the p-tolualdehyde fed and 6.0% of the p-toluic acid fed had been transformed into the following products:
  terephthalic acid: 49.1 g
  4-carboxybenzaldehyde: 6.9 g
  other intermediates: 6.5 g
  heavy by-products: 6.3 g.

COMPARATIVE EXAMPLE

Into the same autoclave as in the preceding examples there was charged:
  p-tolualdehyde: 69.6 g
  p-toluic acid: 123.0 g
  various oxygenated derivatives: 3.0 g
  water: 105.0 g
  cobalt acetate: 3.48 millimoles.

Thus, the same amount of cobalt catalyst was used as hereabove (11.6 millimoles/kg) but here the molar ratio of water to p-toluic acid was 6.45 instead of 2.54. The minimum concentration of cobalt catalyst to be used in this case is therefore $M=17.8$, i.e. by 6.2 millimoles more than actually present in the charge.

This mixture was heated in the presence of air. Here again, oxygen absorption took place immediately. However, after 45 minutes it fell down to a negligible level: nevertheless, heating at 170° C. was continued. After 300 minutes of reaction, the oxygen absorption amounted to only 10.0 liters. The reaction mixture was then treated and analyzed as described in Example 8. It was thus determined that 90.1% of the p-tolualdehyde fed has been transformed into the following products:
  terephthalic acid: 3.7 g
  p-toluic acid: 53.5 g
  4-carboxybenzaldehyde: 3.3 g
  other intermediates: 0.7 g
  heavy by-products: 6.6 g.

It can be seen that p-tolualdehyde has been transformed mainly into p-toluic acid without significant formation of terephthalic acid.

EXAMPLE 10

Into the same autoclave as in the preceding examples there was charged:
  p-toluic acid: 214.3 g
  various oxygenated derivatives: 10.7 g
  water: 75.0 g
  cobalt acetate: 1.74 millimoles
  manganese acetate: 1.50 millimoles.

Thus, in this example no p-xylene nor p-tolualdehyde were used. The mole ratio of water to p-toluic acid (y) was 2.64 and the mole fraction of manganese in the catalyst (x) was 0.46 as in Example 1. The minimum concentration of catalyst to be used as calculated from equation (1) is $M=3.3$ millimoles/kg. Actually, in the present example, the concentrations of catalyst was 3.24 millimoles for 300 g of reaction mixture or 10.8 millimoles/kg, i.e. about three times the limiting amount.

This mixture was heated in the presence of air under the same conditions as in Example 1. In this case again, the reaction started spontaneously. After 180 minutes of reaction 19.4 liters of oxygen had been absorbed and the reaction was discontinued by cooling. The autoclave was then opened and the precipitate contained therein was treated and analyzed as described in Example 1. It was thus determined that 33.2% of the p-toluic acid fed had been transformed into the following products:
  terephthalic acid: 75.5 g
  4-carboxybenzaldehyde: 6.1 g
  other intermediates: 1.8 g
  heavy by-products: 0.1 g.

The net yield of terephthalic acid based on p-toluic acid transformed is 87 mole %. However, taking the intermediate oxidation products as 4-carboxybenzaldehyde into account, the actual yield in terephthalic acid, as would be obtained in a continuous process where intermediates are recycled, can be estimated to be 97 mole %.

This example clearly demonstrates that by the process of the present invention p-toluic acid can be oxidized efficiently and in high yield into terephthalic acid even in the absence of p-xylene or any other easily oxidizable compound as promoter.

EXAMPLE 11

Into the same autoclave as in the preceding examples, there was charged:
  p-xylene: 3.0 g
  p-toluic acid: 142.6 g
  various oxygenated derivatives: 4.4 g
  water: 150.0 g
  manganese acetate: 1.05 millimoles
  cobalt acetate: 1.05 millimoles.

Thus, in this example water amounted to 50 wt % of the initial mixture: y was 7.95 and x was obviously 0.50. By application of equation (1), the minimum concentration of catalyst to be used is $M=4.9$. Actually, in the present example, the concentration of catalyst was 7.0 millimoles/kg, i.e. by 2.1 millimoles in excess over the limiting amount.

Air was admitted into the reactor at a flow rate of 110 liters per hour under a pressure of 20 kg/cm$^2$ and the mixture was heated while stirring. When the temperature was about 170° C., a minute amount of t-butylhydroperoxide was added to help the reaction to start. As a result, oxygen absorption took place immediately. The temperature then increased rapidly and was maintained at 185° C. by controlled cooling. After 300 minutes of reaction, the oxygen absorption amounted to 23.5 liters. The reaction was then discontinued and the resulting mixture was treated and analyzed as in Example 1. It was thus determined that 95.0% of the p-xylene fed and 40.3% of the p-toluic acid fed had been transformed into the following products:
  terephthalic acid: 53.5 g
  4-carboxybenzaldehyde: 5.0 g
  other intermediates: 1.6 g
  heavy by-products: 1.6 g.

COMPARATIVE EXAMPLE 1

The same experiment as in the preceding example was exactly repeated except that the half amount of each metal catalyst was used. The total concentration of catalyst was therefore 3.5 millimoles/kg, i.e. by 1.4 millimoles lower than the limiting amount.

This mixture was heated in the presence of air under exactly the same conditions as in the above example. No oxygen absorption took place at all by maintaining this mixture at 185° C. for 160 minutes, despite too successive additions of t-butylhydroperoxide to help the reaction to start.

By considering the results obtained in the above example where active and substantial oxidation took place in the presence of large amounts of water, it appears clearly that such an oxidation is only feasible when the proper amount of catalyst is used as specified in the present invention.

COMPARATIVE EXAMPLE 2

The same experiment as in Example 11 was repeated except that benzoic acid was substituted for a part of p-toluic acid. The actual composition of the charge was the following:
  p-xylene: 3.0 g
  p-toluic acid: 44.5 g
  benzoic acid: 93.9 g
  various oxygenated compounds: 2.0 g
  water: 156.6 g
  manganese acetate: 1.05 millimoles
  cobalt acetate: 1.05 millimoles.

In this example y was 26.59; thus, by application of equation (1), the minimum concentration of catalyst to be used for ensuring oxidation of the above mixture is 10.7 millimoles/kg, i.e. more, by 3.7 millimoles, than the amount actually present. By contrast, if benzoic acid had the same effect as p-toluic acid for ensuring oxidation in aqueous medium, it should be taken into account in the calculation of y and M. In this case, we would have
$y=(156.6/18.02)/(44.5/136.15+93.9/122.12)=7.93$, i.e. the same value as calculated for y in Example 11, where active oxidation took place.

The above mixture was heated at 185° C. under the same conditions as in Example 11 and here again some t-butylhydroperoxide was added to help initiation. However, no significant oxidation took place even upon continuing heating for 180 minutes. This demonstrates that, at least, benzoic acid has not the same activity as p-toluic acid to promote oxidation in the presence of water as carried out in the process of the present invention.

COMPARATIVE EXAMPLE 3

The same experiment as in Example 11 was repeated except that acetic acid was substituted for a part of p-toluic acid. The actual composition of the charge was the following:
  p-xylene: 3.0 g
  p-toluic acid: 52.7 g
  acetic acid: 55.2 g
  various oxygenated compounds: 1.3 g
  water: 187.8 g
  manganese acetate: 1.05 millimoles
  cobalt acetate: 1.05 millimoles.

In this example y was 26.92 so that M was 10.8, i.e. about the same as in the preceding comparative example. Here again, if acetic acid had the same promoting effect as p-toluic acid for oxidation in aqueous medium, it should be taken into account for the calculation of y and M. In this case we would have $y=(187.2/18.02)/(52.7/136.15+55.2/60.05)=7.95$, i.e. exactly the same value as in Example 11.

The above mixture was heated at 185° C. under the same conditions as in Example 11 and here again some t-butylhydroperoxide was added to help initiation. After 300 minutes of reaction the oxygen absorption amounted to only 3.8 liters. This result demonstrates once again that the promoting effect of p-toluic acid as it appears in the process of the invention is not displayed by other carboxylic acids, i.e. is specific of p-toluic acid.

EXAMPLE 12

Into the same autoclave as in the preceding examples, there was charged:
- p-xylene: 6.0 g
- p-toluic acid: 183.3 g
- various oxygenated derivatives: 5.7 g
- water: 105.0 g
- manganese acetate: 1.80 millimoles.

Here, y=4.33 and, as manganese was used as sole catalyst, x=1.00. Therefore, by application of equation (1), the minimum concentration of manganese to be used in this case is M=3.6 millimoles/kg. Actually, in the present example, the concentration of manganese was 6.0 millimoles/kg, thus well in excess over the limiting amount.

This mixture was heated in the presence of air exactly under the same conditions as in Example 11 except that temperature was maintained at 170° C. instead of 185° C. After 305 minutes of reaction, the oxygen absorption amounted to 21.2 liters. Upon treating and analyzing the resulting reaction mixture as in the preceding examples, it was determined that about 96% of the p-xylene fed and 29.9% of the p-toluic acid fed had been transformed into the following products:
- terephthalic acid: 44.8 g
- 4-carboxybenzaldehyde: 14.2 g
- other intermediates: 0.9 g
- heavy by-products: 1.2 g.

COMPARATIVE EXAMPLE

The same amounts of compounds as in the preceding example were charged into the reactor except that only 0.60 millimoles of manganese acetate was used as catalyst. The concentration thereof in the mixture was therefore 2.0 millimoles/kg, i.e. by 1.6 millimole lower than the limiting amount. As a result, no oxygen absorption took place upon heating the mixture for 60 minutes in the presence of air under the same conditions as in the preceding example, even after addition of t-butylhydroperoxide to help initiation.

EXAMPLE 13

Into the same autoclave as in the preceding examples, there was charged:
- p-xylene: 6.0 g
- p-toluic acid: 218.3 g
- various oxygenated derivatives: 2.2 g
- water: 73.5 g
- cobalt acetate: 3.48 millimoles.

Thus, in this example it is cobalt which was used as sole catalyst, i.e. x=0. On the other hand, y was 2.54. By application of equation (1), the minimum concentration of cobalt to be used in this case is M=7.0 millimoles/kg. Actually, in the present example, the concentration of cobalt was 11.6 millimoles/kg.

Air was admitted into the reactor at a flow rate of 90 liters per hour under a pressure of 20 kg/cm² and the mixture was heated up to a temperature of 170° C. While heating, the reaction started spontaneously and was continued for 240 minutes. At the end of the reaction, the oxygen absorbed amounted to 29.8 liters. Upon treating and analyzing the reaction mixture as described in Example 1, it was determined that 89.3% of the p-xylene fed and 37.0% of the p-toluic acid fed had been transformed into the following products:
- terephthalic acid: 81.5 g
- 4-carboxybenzaldehyde: 6.8 g
- other intermediates: 1.2 g
- heavy by-products: 3.0 g.

COMPARATIVE EXAMPLE

The same amounts of compounds as in the preceding example were charged into the reactor except that only 0.90 millimole of cobalt acetate was used as catalyst. The concentration thereof in the mixture was therefore 3.0 millimoles/kg, i.e. by 4.0 millimoles lower than the limiting amount. As a result, no oxygen absorption took place upon heating this mixture for 240 minutes in the presence of air under the same conditions as in the preceding example, even after repeated additions of t-butylhydroperoxide.

It is to be understood that the foregoing description of the fundamental novel features of the present invention is merely illustrative of preferred embodiments. Those skilled in the art will appreciate that many variations may be made. For example, in carrying out the process of the present invention, there may be added to the reaction mixture one or another extraneous compound used as activator in other processes, e.g. an aldehyde or a ketone or still a bromine-containing compound. Such additives may even be advantageous with respect to e.g. the reaction rate. These variations, modifications or changes may be made within the scope of the following claims without departing from the spirit thereof.

What is claimed is:

1. A process for preparing terephthalic acid which comprises the steps of:
   (a) oxidizing a substantially homogeneous aqueous liquid reaction mixture comprising
   at least one oxidizable terephthalic acid precursor selected from the group consisting of p-toluic acid, and mixtures of p-toluic acid and an oxidizable compound selected from the group of p-xylene, partially oxidized p-xylene derivatives, and mixtures thereof,
   an amount of at least 5% by weight of water which is sufficient to obtain a workable slurry,
   an amount of an oxidation catalyst comprising at least one catalytically-active metal compound selected from the group consisting of manganese compounds, cobalt compounds, and mixtures thereof which is sufficient to provide an amount of catalytically-active compound between a minimum amount of M millimoles of the catalytically-active metal compound per kg of the liquid reaction mixture, wherein M is defined by the following equation $$M = \frac{y(x + A) + Bx}{Cx + D}$$

wherein
   y represents the molar ratio of water/p-toluic acid in the reaction mixture,
   x represents the molar ratio of manganese/total amount of manganese+cobalt in the catalyst composition, i.e., Mn/(Mn+Co)
   A equals about 0.002,
   B equals about 10.9,
   C equals about 4.35, and
   D equals about 0.0724,
   and a maximum of about 40 millimoles of catalytically-active compound per kg of the reaction mixture, with a molecular oxygen-containing gas at a reaction temperature of from about 140° C. to about 220° C. and at a pressure sufficient to maintain at least part of the water in the liquid phase at the reaction temperature; and (b) recovering an oxidized mixture containing the terephthalic acid.

2. The process as defined in claim 1, wherein

A equals about 0.200±0.031;
B equals about 10.9±1.3,
C equals about 4.35±0.17, and
D equals about 0.0724±0.0117.

3. The process as defined in claim 1, wherein the amount of water in the liquid reaction mixture is from about 5 to about 80% by weight of the reaction mixture.

4. The process as defined in claim 3, wherein the amount of water in the liquid reaction mixture is from about 5 to about 75% by weight of the reaction mixture.

5. The process as defined in claim 3, wherein the amount of water in the liquid reaction mixture is from about 10 to about 75% by weight of the reaction mixture.

6. The process as defined in claim 3, wherein the amount of water in the liquid reaction mixture is from about 10 to about 60% by weight of the reaction mixture.

7. The process as defined in claim 1, wherein the reaction mixture further comprises an amount of from 0 to 100% relative to the amount of water of an inert organic solvent.

8. The process as defined in claim 7, wherein the organic solvent comprises acetic acid.

9. The process as defined in claim 1, wherein the reaction temperature is from about 150° C. to about 190° C.

10. The process as defined in claim 1, wherein the reaction pressure is from about 5 to about 40 kg/cm$^2$.

11. The process as defined in claim 1, wherein the amount of oxidation catalyst is sufficient to provide an amount of catalytically-active compounds which is between the minimum amount as defined in claim 1 and about 30 millimoles per kg of the reaction mixture.

12. The process as defined in claim 1, wherein the catalyst comprises a mixture of a manganese compound and a cobalt compound.

13. The process as defined in claim 12, wherein x is from about 0.1 to about 0.9.

14. The process as defined in claim 1, wherein the catalytically-active metal compound is a metal salt of a carboxylic acid.

15. The process as defined in claim 1, wherein the catalyst further comprises a compound of a metal selected from the group consisting of nickel, lead, and cerium.

16. The process as defined in claim 1, wherein the molar ratio of p-toluic acid to p-xylene is from about 3 to about 15.

* * * * *